United States Patent [19]

Lenk et al.

[11] Patent Number: 5,082,664
[45] Date of Patent: Jan. 21, 1992

[54] PROSTAGLANDIN-LIPID FORMULATIONS

[75] Inventors: Robert P. Lenk, Lambertville, N.J.; Michelle L. Tomsho, Levittown, Pa.; Robert L. Suddith, Robbinsville; Robert J. Klimchak, Flemington, both of N.J.

[73] Assignee: The Liposome Company, Inc., Princeton, N.J.

[21] Appl. No.: 195,228

[22] Filed: May 18, 1988

Related U.S. Application Data

[63] Continuation-in-part of Ser. No. 53,305, May 22, 1987, abandoned.

[51] Int. Cl.$^5$ .............................................. A61K 37/22
[52] U.S. Cl. .................................. 424/450; 428/402.2; 436/829; 264/4.3
[58] Field of Search .............. 424/450; 428/402.2; 436/829; 264/4.3

[56] References Cited

U.S. PATENT DOCUMENTS

| | | | |
|---|---|---|---|
| 3,993,754 | 11/1976 | Rahman et al. | 424/177 |
| 4,145,410 | 3/1979 | Sears | 424/19 |
| 4,229,360 | 10/1980 | Schneider et al. | 260/403 |
| 4,235,871 | 11/1980 | Papahadjopoulos et al. | 424/19 |
| 4,370,349 | 1/1983 | Evans et al. | 424/365 |
| 4,493,847 | 1/1985 | Mizushima et al. | 424/317 |
| 4,522,803 | 6/1985 | Lenk et al. | 424/1.1 |
| 4,588,578 | 5/1986 | Fountain et al. | 424/1.1 |

FOREIGN PATENT DOCUMENTS

| | | |
|---|---|---|
| 0150732 | 8/1985 | European Pat. Off. |
| 61-100518 | 5/1986 | Japan . |
| WO86/00238 | 1/1986 | PCT Int'l Appl. . |
| WO86/01102 | 2/1986 | PCT Int'l Appl. . |
| WO86/01103 | 2/1986 | PCT Int'l Appl. . |
| 2050287A | 1/1981 | United Kingdom . |
| 0150732A2 | 8/1985 | United Kingdom . |
| 85/00968 | 3/1985 | |
| 85/04578 | 10/1985 | World Int. Prop. O. . |
| 86/00238 | 1/1986 | World Int. Prop. O. . |
| 86/01103 | 2/1986 | World Int. Prop. O. . |
| 87/00043 | 1/1987 | World Int. Prop. O. . |

OTHER PUBLICATIONS

Bangham et al., "Diffusion of Univalent Ions Across the Lamellae of Swollen Phospholipids", 1965; J. Mol. Biol., 12:238-252.

Batzri et al., "Single Bilayer Liposomes Prepared Without Sonication", 1973; Biochim. Biophys. Acta., 298:1015-1019.

Hoshi et al., "Prostaglandin E, Incorporated in Lipid Microspheres in the Treatment of Peripheral Vascular Diseases and Diabetic Neuropathy", 1986; Drugs Exptl. Clin. Res., XII(8):681.

Mizushima et al., "Prostaglandin $E_1$ is More Effective, When Incorporated in Lipid Microspheres for Treatment of Peripheral Vascular Diseases in Man", 1983; J. Pharm. Pharmacol. 35:666-667.

Moncada et al., "Prostaglandins, Prostacyclin, and Thromboxane $A_2$"; The Pharmacol. Basis of Therapeutics, MacMillan Pub., Inc., NY, pp. 668-676.

Papahadjopoulos et al., "Phospholipid Model Membranes", 1968; Biochim. Biophys. Acta., 135:624-638.

Shulkin et al., "Lyophilized Liposomes: A New Method for Long-Term Vesicular Storage", 1984; J. Microencapsulation, 1(1):73.

Primary Examiner—William R. Dixon, Jr.
Assistant Examiner—Anthony J. Green
Attorney, Agent, or Firm—Allen Bloom; Catherine L. Kurtz; Ronald G. Ort

[57] ABSTRACT

A liposome composition and methods for making same are disclosed, such compositions comprise an arachidonic acid metabolite such as a prostaglandin, preferably prostaglandin $E_1$, a lipid, and a drying protectant such as a saccharide. The liposomes may be loaded with prostaglandin passively, or using a transmembrane concentration gradient, preferably using a transmembrane pH gradient. Using this transmembrane loading technique, trapping efficiencies of 50% to 100% are achieved, and the release rate of the prostaglandin from the liposomes is reduced. The liposome size is maintained after lyophilization and reconstitution.

51 Claims, No Drawings

PROSTAGLANDIN-LIPID FORMULATIONS

RELATED U.S. APPLICATION DATA

This application is a continuation-in-part of copending patent application Ser. No. 053,305, filed May 22, 1987 now abandoned.

BACKGROUND OF THE INVENTION

The present invention is directed to formulations and methods for making arachidonic acid metabolite-associated liposomes. Such arachidonic acid metabolites also include their structural analogs, synthetic enzyme inhibitors, and arachidonic acid itself. One class of such arachidonic acid metabolite is the group of bioactive agents known as the prostaglandins. This invention specifically discloses prostaglandin-associated liposomes, using prostaglandin $E_1$. The term prostaglandin also includes synthetic compounds structurally related to the naturally occurring prostaglandins.

The prostaglandins are substances found in essentially all human tissues and body fluids and produce a broad spectrum of effects embracing practically every biological function. These substances are derived from the 20-carbon essential fatty acids (arachidonic acid, the most abundant precursor) and are biologically synthesized into structures such as the 20-carbon prostaglandin subclass $E_1$ ("$PGE_1$") shown below:

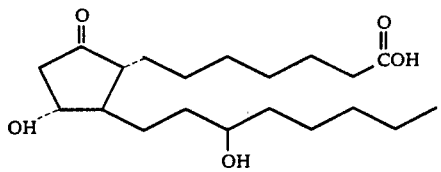

Other prostaglandin subclasses are designated by letters and distinguished by substitutions on the cyclopentane ring. Such subclasses are the prostaglandin E and $F_\alpha$ series, which have been most intensively studied, with the subclasses A, B, and C being derivatives of the E's. Prostaglandins A through F are considered the "primary prostaglandins"; the structures of prostaglandins $G_2$ and $H_2$ (the cyclic endoperoxides) and thromboxanes $A_2$ and $B_2$ have been more recently elucidated (Goodman et al., eds., The Pharmacological Basis of Therapeutics, MacMillan Publishing Co., New York, pp. 668-676). Other bioactive agents that may be used in the invention are prostacyclines and leukotrienes.

The prostaglandins have diverse physiological actions such as vasodilative action, improvement of peripheral blood circulation, and antilipolysis. The prostaglandins are therapeutically indicated in many conditions, including but not limited to ductus arteriosus, stimulation of uterine contractions leading to induction of labor at term as well as abortion, treatment of bronchial asthma, and suppression of gastric ulceration in animals. They are also used in the prophylaxis of arteriosclerosis.

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

The original liposome preparation of Bangham et al. (J. Mol. Biol., 1965, 13:238-252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (Biochim. Biophys, Acta., 1968, 135:624-638), and large unilamellar vesicles.

Unilamellar vesicles may be produced using an extrusion apparatus by a method described in Cullis et al., PCT Application No. WO 86/00238, Jan. 16, 1986, entitled "Extrusion Technique for Producing Unilamellar Vesicles" incorporated herein by reference. Vesicles made by this technique, called LUVETS, are extruded under pressure through a membrane filter. Vesicles may also be made by an extrusion technique through a 200 nm filter, such vesicles are known as $VET_{200}s$.

Another technique used to form liposomes is the "reverse phase evaporation" (REV) process of Papahadjopoulos (U.S. Pat. No. 4,235,871, issued Nov. 25, 1980). Such process forms oligolamellar lipid vesicles wherein the aqueous material to be encapsulated is added to lipids in organic solvent, forming an water-in-oil type emulsion. The organic solvent is removed, forming a gel. The gel is dispersed in aqueous medium converting it to a suspension. Yet another technique is the detergent-dialysis process (Enoch et al., 1979, Proc. Natl. Acad. Sci., 76:145). In this process, lipid is mixed with a detergent such as deoxycholate in aqueous solution, sonicated, and the detergent removed by gel filtration. A further technique is the ethanol infusion technique of Batzri et al. (1973, Biochim. Biophys. Acta., 298:1015), for forming small unilamellar vesicles, whereby an ethanol solution of lipid is injected into the desired aqueous phase, forming liposomes of about 30 nm to about 2 um in diameter. The residual ethanol may then be removed by rotoevaporation.

Another class of liposomes that may be used in the present invention are those characterized as having substantially equal lamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,588,578 to Fountain, et al. and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies". The relevant portion of these references is incorporated herein by reference.

In a liposome-drug delivery system, a bioactive agent such as a drug is entrapped in or associated with the liposome and then administered to the patient to be treated. For example, see Rahman et al., U.S. Pat. No. 3,993,754; Sears, U.S. Pat. No. 4,145,410; Papahadjopoulos et al., U.S. Pat. No. 4,235,871; Schnieder, U.S. Pat. No. 4,114,179; Lenk et al., U.S. Pat. No. 4,522,803; and Fountain et al., U.S. Pat. No. 4,588,578.

The use of liposomes to administer drugs has raised problems with regard to both drug encapsulation and drug release during therapy. With regard to encapsulation, there has been a continuing need to increase trapping efficiencies so as to minimize the lipid load presented to the patient. In addition, high trapping efficiencies mean that only a small amount of drug is lost during the encapsulation process, an important advantage when dealing with expensive drugs. As to drug release, many drugs have been found to be rapidly released from liposomes after encapsulation. Such rapid release diminishes the beneficial effects of liposome encapsulation. Accordingly, there have been continuing efforts by those skilled in the art to find ways to reduce the rate of release of drugs from liposomes.

In addition to these problems with encapsulation and release, there is the overriding problem of finding a commercially acceptable way of providing drug-containing liposomes to the clinician. Although the production and loading of liposomes on an "as needed" basis is an acceptable procedure in an experimental setting, it is, in general, unsatisfactory in a clinical setting. Accordingly, there is a significant and continuing need for methods whereby liposomes, with or without encapsulated drugs, can be shipped, stored and in general moved through conventional commercial distribution channels without substantial damage.

SUMMARY OF THE INVENTION

The present invention discloses an encapsulation procedure which significantly improves both the partitioning and subsequent entrapment of the prostaglandin into the liposome, and the stability of the liposome-entrapped prostaglandin formulation. More specifically, the liposomes are formed initially in an aqueous solution of relatively basic pH, and the pH is later adjusted to a relatively acidic pH. Upon acidification of the liposomal external solution the prostaglandin becomes associated with the liposomes. Such association may be by partitioning into and through the liposomal membranes. Such a procedure suprisingly results in a 50 to 100% entrapment of the prostaglandin in the liposomes. The buffering system used to achieve this entrapement, is therefore called a partition-enhancing buffer.

The resulting liposomes are size-reduced to a homogenous size distribution. Following pH adjustment, the resulting solution can be dehydrated or lyophilized and stored until use, when it may be rehydrated using an aqueous solution. Such a process requires the addition of a drying protectant prior to the drying process (dehydration or lyophilization) which maintains the liposome particle size after rehydration. In the absence of such a drying protectant, the forces that maintain the liposome integrity when in an aqueous suspension are removed. Such a protectant may be a saccharide such as sucrose, dextrose, maltose, mannose, galactose, raffinose, trehalose, or lactose. Mannitol may be used in conjunction with any of the saccharides. Other substances such as albumin, dextran, or poly (vinyl alcohol) may also be used.

Inexpensive lipids can be employed in the present invention, and trapping efficiencies of about 50% and above (preferably 80-100%) for a wide range of lipid compositions are readily achieved. Another unique advantage of this pH-driven uptake process is that there is a reduction in the rate at which the drug is released from the liposomes resulting in increased stability compared to liposomes with passively entrapped (no pH gradient) prostaglandin. This reduced rate of release of entrapped bioactive agent is mediated by the pH difference of the aqueous solutions (the partition-enhancing buffering system) used in the preparations. Thus, the partition-enhancing buffer or buffering system aids in the retention of the prostaglandin in the liposomes.

Thus, the present invention discloses a liposome composition which comprises an arachidonic acid metabolite which is preferably a prostaglandin, a lipid, a drying protectant, and a partition-enhancing buffer or buffering system. The prostaglandin is preferably prostaglandin $E_1$. The liposomes can possess a transmembrane chemical potential such as a concentration gradient, which is preferably a pH gradient. The partition-enhancing buffer system comprises two solutions, one being a solution of a drying protectant, preferably a saccharide solution, and the second, preferably a citric acid solution. The saccharide solution is preferably dextrose, sucrose, or maltose, any of which may be combined with mannitol. Other protectants that may be used include dextran, poly (vinyl alcohol), or albumin. The pH of the protectant solution is preferably relatively basic, at about pH 3 to about pH 11, most preferably about pH 7. The drying protectant solution, preferably a saccharide solution, is present in about 5% to about 20% by weight, most preferably about 10% to about 12%. The liposome solution can then be size-reduced by, for example by, an extrusion or homogenization procedure. The resulting solution can be dried by a dehydration or a lyophilization procedure. The citric acid solution is preferably of pH about 2.5 to about 4.5, more preferably pH 3.0.

The lipid preferably comprises phospholipid, more preferably phosphatidylcholine, most preferably egg phosphatidylcholine. The liposomes are preferably from 100 to 500 nm in diameter, most preferably about 200 nm. The entrapment of the prostaglandin in the liposomes is about 50 to about 100%, more particularly about 60 to 100%. The liposomal composition may be injected into a patient intravenously. Pharmaceutical compositions of the liposomal prostaglandins may be made by their admixture with a pharmaceutical carrier or diluent.

The lipid to prostaglandin weight ratio in the compositions of the present invention are about 150:1 to about 1000:1, more preferably about 300:1 to 800:1, most preferably about 600:1. The liposomal prostaglandin compositions of the invention may also be lyophilized.

The liposomes of the invention may be prepared by associating the prostaglandin with the lipid by means of a transmembrane pH gradient. This gradient may be obtained by first forming the liposomes in a basic aqueous medium, adding the prostaglandin to the aqueous suspension, and then acidifying the external (aqueous) medium of the liposomes. The basic external medium may be a saccharide solution, while the acidification may be achieved by use of an acidic solution such as a citric acid solution.

The liposomes of the invention may be size reduced to a uniform size distribution by extruding them through filters having straight through or tortuous paths, or by homogenization. This size-reduction step is preferably performed prior to the addition of the prostaglandin, the drying step, and the formation of the transmembrane pH gradient.

Alternatively, the liposomes of the invention may be prepared using a passive loading technique, whereby the lipid is admixed with an aqueous solution of the drying protectant which also contains the prostaglandin. Such lipid may be in the form of a dried lipid film. Such passively-loaded liposomes may also be lyophilized.

DETAILED DESCRIPTION OF THE INVENTION

The liposomes of this invention present arachidonic acid metabolites, specifically prostaglandins, in association with liposomes. Such association includes the entrapment of the prostaglandin in the liposome, and the potential association of the prostaglandin with the external or internal membrane surface of the liposome.

As discussed above, the liposomes of the invention may be formed by any of the known methods for forming liposomes, but preferably they are loaded with bioactive agent according to the procedures disclosed in Bally et al., for ionizable antineoplastic agents, PCT Application No. 86/01102, Feb. 27, 1986 and incorporated herein by reference. This technique allows the loading of liposomes with ionizable bioactive agents wherein a transmembrane concentration gradient is created across the membranes of the liposomes and the drug is loaded into the liposomes by means of this gradient. The transmembrane concentration (ion) gradient is generated by creating a concentration gradient for one or more charged species (e.g., $Na^+$, $Cl^-$, $K^+$, $Li^+$, $H^+$) across the liposome membranes. Preferably, these ion gradients are pH ($H^+$) gradients. These pH gradients can drive the uptake of ionizable bioactive agents (drugs, such as prostaglandins) across the liposome membranes.

According to the present invention, liposomes are prepared which encapsulate a first aqueous medium (relatively acidic or basic). In the case of $PGE_1$, it has been found that an encapsulation scheme where the first aqueous medium is relatively basic (with respect to the second aqueous medium) results in highest entrapment.

To create the concentration gradient, the first external medium is adjusted (by adjustment of the external pH), or a second external medium is added (which, for example, may be either relatively basic or acidic with respect to the original external medium). In the case of $PGE_1$ entrapment, the addition of a second external medium that is acidic relative to the first external medium is preferable. If either the first or second external medium contains an ionizable bioactive agent such as an ionizable prostaglandin, the transmembrane pH ($H^+$) gradient (inside basic with respect to the outside) will partition the drug into the liposomes such that the free vesicle-associated bioactive agent ratios reflect the $[H^+]_{in}$ $[H^+]_{out}$ ratios. An ion gradient remains in the liposomes even after the loading has been completed.

The transmembrane pH gradient loading method can be used with essentially any prostaglandin which can exist in an ionizable state when dissolved in an appropriate aqueous medium. In the case of prostaglandins, such an ionizable group may be the carboxyl group on the fatty acid chain (See I above). Preferably the prostaglandin is also relatively lipophilic so that it will partition into the liposome membranes. Examples of some of the prostaglandins which can be loaded into liposomes by this method and therefore may be used in this invention include $PGE_1$, $PGE_2$, PGG, and PGF, among others.

In addition to loading a single prostaglandin into liposomes, the pH gradient loading method can be used to load multiple prostaglandins either simultaneously or sequentially.

In general, any of the methods for forming liposomes mentioned in the Background of the Invention may be used in the practice of the invention, but methods that form unilamellar vesicles are preferred, most preferably large unilamellar vesicles. Two methods for forming these unilamellar vesicles are preferred: the first technique, is the association of bioactive agent (drug, specifically prostaglandin) with the lipid in ethanol similar to the technique of Batzri et al., (1973, Biochim. et Biophys. Acta., 298:1015) using the transmembrane concentration gradient as disclosed in Bally et al. (supra.) to load the bioactive agent. In this technique, lipid and prostaglandin are co-dissolved in an aqueous-miscible organic solvent such as ethanol at 5% the total aqueous volume, then added slowly to a first aqueous solution. The first aqueous solution may be an aqueous solution such as, preferably, a solution of the drying protectant, or a buffer, for example, such as citrate or phosphate. Such a buffer solution may additionally comprise a drying protectant. The drying protectant may comprise a saccharide such as sucrose, maltose, lactose or dextrose, or a combination of saccharides such as either sucrose, maltose, lactose or dextrose with mannitol. Maltose is preferably used. Other saccharides may include, for example, mannose, galactose, raffinose, or trehalose. Alternatively, other protectants such as dextran, albumin, and poly(vinyl alcohol) may also be used. The pH of this first aqueous solution is relatively basic (compared to that of the second aqueous solution, see below), e.g., about 3.0 to about 11.0, most preferably about 7.0. In other words, in comparison to the second aqueous solution, the first is more basic. This buffer may alternatively be relatively acidic (as compared to that of the second aqueous solution).

The resulting single-phase liposome solution is size-reduced to a homogenous population, for example, by extrusion through a filter, preferably of 0.2 micron pore size, the filter being of either the straight path or tortuous path type. Such a population may be formed by the extrusion procedures of Cullis et al., PCT Publication No. 86/00238, Jan. 16, 1986, relevant portions of which are incorporated herein by reference. Such extrusion procedures, wherein the liposomes are passed through a filter under pressure, allow the formation of homogenous populations of liposomes with regard to size. The extrusion may be performed by one or several passes through a filter; for example a straight-through membrane filter (e.g., a Nucleopore polycarbonate filter) or a tortuous path filter (e.g., a Nucleopore membrafil filter (mixed cellulose esters) of 0.2 um size). When the liposomes are passed more than one time through the filter, the number of passes required will be determined by that necessary to achieve the desired liposome size, i.e., preferably about 0.20 um.

The filter sizes used in the invention are chosen according to the desired size of the final liposome product. In the present invention, for example, liposomes having an average diameter of about 0.20 um are preferred.

The liposomes of the present invention are preferably less than about 500 um in diameter, and are preferably 100 nm to 300 nm in diameter. In the present invention, liposomes which are of about 200 nm are most preferred since liposomes of about this size are known to pass through the capillary bed of the lung and are therefore able to pass through to other organs and tissues. Therefore, a filter having a pore size of about 0.20 um is chosen for use in the extrusion step.

Other methods for size-reducing the liposomes to a homogenous size distribution as defined hereinabove are ultrasonic exposure, the French Press technique, hydrodynamic shearing, homogenization using for example, a colloid mill or Gaulin homogenizer, or other size reduction techniques. For example, when the Gaulin homogenization method is used, the liposomes to be sized are continuously cycled from a reservoir, for example, into the homogenizer at a flow rate of 2 L/min. so that for a 1 liter batch, the liposomes are recycled for 4 minutes at about 14,000 psi. A heat exchanger may be used to maintain the batch temperature below about 30° C.

The resulting size-reduced liposomes are homogenous with regard to size. For example, the liposomes are of Gaussian distribution about a mean of 200 nm, with a range of about 20 to about 500 nm.

The resulting size-reduced product may be diluted with additional aqueous solution, dried, and stored until use, or alternatively, the pH may be changed to load the drug via the transmembrane pH gradient. The sizing procedure, however, must be performed prior to the final pH adjustment.

The second and more preferable method for forming the liposomes of the invention is, using the ethanol injection method of Batzri et al. (supra.), to first admix the lipid with a preservative, for example butylated hydroxytoluene (BHT), in ethanol at 5% the total aqueous volume, then add this mixture slowly to a first aqueous medium. This first aqueous medium may be any of those described hereinabove, but is preferably a saccharide solution such as, for example, maltose. The pH of this first aqueous solution is basic relative to the second aqueous solution, and is preferably pH 3.0 to about 11.0, most preferably about pH 7.0. This process forms liposomes entrapping the saccharide solution.

The resulting liposome solution is size-reduced to a homogenous population by any of the methods described hereinabove, but preferably by the Gaulin homogenization method as described. Liposomes of about 20-500 nm, more preferably having a size diameter of about 100 nm to about 500 nm are formed, preferably of a mean size of 200 nm.

The resulting size reduced liposome product may be sterile filtered through a 0.2 um Millipak filter (Millipore, Inc., Bedford, MA). The resulting size-reduced and filtered liposomes are then admixed with the bioactive agent which has been dissolved in ethanol. For example, the prostaglandin, dissolved in ethanol, is added to a stirring solution of liposomes. The prostaglandin-liposome product may then be sterile filtered through a 0.2 um filter. The product may also be diluted with additional aqueous solution, and/or dried (dehydrated) and stored until use. In the preferred embodiments, the size-reduced product is filled into vials, lyophilized, and stored until use.

Immediately prior to use, the lyophilized product may be reconstituted with an aqueous solution having a pH relatively acidic or basic to the first aqueous medium. This second aqueous medium is preferably relatively acidic. The addition of this aqueous medium forms the pH gradient.

Regardless of the liposome forming procedure used, to form the transmembrane pH gradient, an external medium comprising an aqueous solution of a second pH (a second external medium) having a relatively acidic pH with respect to the first external medium is added to the liposome solution. The pH of this second aqueous solution is generally about 2.5 to about 4.5., preferably about 3.0 to 3.5, most preferably about pH 3.0. Upon adjustment of the first external medium by, for example, addition of this second aqueous solution, the pH of the liposome solution is about 3.0 to about 4.5., preferably about 3.0. Alternatively, if the first aqueous solution was relatively acidic, the second aqueous solution would be relatively basic.

Such an adjustment of the pH of the external medium will partition the bioactive agent (prostaglandin) into and through the liposome membranes, effectively loading the prostaglandin into the liposomes. Using the partition-enhancing buffer pair of the present invention with the pH gradients described above, entrapment efficiency of the prostaglandin is about 50 to 100%, more specifically 60 to 100%, and most preferably 80 to 100%.

Without being bound by any theory, it is believed that the role of the drying protectant in the formulation is to maintain the size and integrity of the liposomes during the drying process, and after rehydration. When the drying protectant is omitted from the liposome formulation, the rehydrated liposomes have a low entrapment efficiency (around about 30% and less), and the liposome size following the lyophilization is not maintained.

The dehydration or lyophilization procedure may be performed either prior to or following the establishment of the pH gradient. Preferably, it is performed prior to the establishment of the pH gradient, and most preferably, the first aqueous medium is relatively basic and the second relatively acidic. In this case, the rehydration of the dried liposome-prostaglandin formulation is performed using the second (relatively acidic) solution, whereupon the concentration gradient is established, effectively loading the prostaglandin into the liposomes. If the acidification is performed prior to the dehydration or lyophilization, this second solution may also contain drying protectant and preservatives such as BHT, and/or ethylenediaminetetraacetic acid (EDTA). The pH of this second aqueous (acidification) solution is from about 1.5 to about 3.5, preferably about 3.0. If, however, the acidification is performed subsequent to the dehydration or lyophilization, the rehydration is performed using an aqueous solution at pH about 2.5 to about 4.5, preferably about 3.0, and without the drying protectant. This latter method, i.e., acidifying the solution after the drying step, is preferred.

In both liposome-forming methods, the resulting prostaglandin-associated liposomes may be dehydrated or lyophilized by any method known in the art. This drying procedure requires the addition of a drying protectant to the liposome suspension. This drying protectant prevents the rearrangement of the lipids in the liposome, so that the size and contents are maintained during the drying procedure and through rehydration. Appropriate qualities for such drying protectants are that they be strong hydrogen bond acceptors, and possess stereochemical features that preserve the intramolecular spacing of the liposome bilayer components. It has been found that one group of drying protectant, the saccharide sugars, when included in the liposome formulations, are especially useful at maintaining the liposome particle size after rehydration. This specific group of saccharides comprises, for example, dextrose, sucrose, and maltose, which may be used at about 5 to about 20 percent, preferably at about 10 percent by weight of the aqueous phase. Other saccharides which may be employed are mannose, galactose, raffinose, trehalose, lactose, or triose sugars. Mannitol may be used in conjunction with any of the saccharides, but it has surprisingly been found that when used alone, mannitol does not succeed in maintaining liposome size. Mannitol may be used in concert with the saccharides in about a 0–2% concentration, preferably a 1% concentration. The total concentration of saccharide used ranges from about 5% to about 20%, preferably 10% to 12%, most preferably about 10%. Additional preservatives such as BHT or EDTA in the formulations at, for example, 0.02 mg BHT per ul of ethanol, and, for example, 0.01% EDTA in 10% dextrose may also be included. Other substances such as urea, albumin, dextran, or poly(vinyl alcohol) may also be used.

Upon rehydration of the dehydrated or lyophilized product, an aqueous solution such as distilled water, (if the pH gradient was established prior to lyophilization) may be added. In the case where the liposomes were lyophilized in their original external aqueous solution, rehydration is performed using a second aqueous solution that will establish the pH gradient, as described hereinbelow (one that is relatively acidic or basic). In the preferred method, the pH gradient is established by adding a relatively acidic aqueous solution to the formulation, such as, preferably, citric acid solution. In all cases, reconstitution may proceed at about 20° to 30° C., preferably 25° C., and the solutions diluted as needed and administered.

In the present invention, the term lipid as used herein shall mean any suitable material resulting in a bilayer upon admixture with an aqueous medium such that a hydrophobic portion of the lipid material orients toward the bilayer while a hydrophilic portion orients toward the aqueous phase. Lipids include highly hydrophobic compounds such as triglycerides, sterols such as cholesterol, and amphipathic lipids. The lipids preferred for use in the liposome formulations of the present invention are the phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. In the preferred embodiments, the phospholipid egg phosphatidylcholine (EPC), is used. The liposomes can also contain other steroid components such as coprostanol, cholestanol, or cholestane, and combinations of EPC and cholesterol. The liposomes may also contain glycolipids.

In the case of loading the liposomes via a pH gradient wherein the first external medium is basic, suitable aqueous media include buffers which may include but are not limited to, for example, citric acid, succinic acid, or maleic acid buffers adjusted to pH 3.0 to about 11.0, preferably about pH 7.0. In other cases where the first buffer used is basic, buffers such as phosphate buffer or 0.9% aqueous sodium chloride may be used at pH 7–9. Alternatively, a sodium carbonate or bicarbonate buffer may be used. Other buffered salines may be included in this mixture at about pH 8.0. Such buffered salines include phosphate buffered saline "PBS," tris-(hydroxymethyl)-aminomethane hydrochloride ("tris") buffers, or N-2-Hydroxyethyl Piperazine-N'2-Ethane sulfonic acid ("HEPES"), or glycine. Most preferably, the first aqueous solution is a solution of the drying protectant, i.e., the saccharide solution, for example, about 5 to 20% maltose (preferably about 10% maltose), at pH about 7.0. This solution may also comprise EDTA or a similar preservative (BHT) at any concentration acceptable for pharmaceutical products (preferably about 0.01% EDTA).

To establish the pH gradient, a second external medium is added (preferably after the dehydration step), or the first medium adjusted to preferably an acidic pH. Such second external media that may replace the first external medium may comprise buffers such as, for example, citric acid, lactic acid, or phosphoric acid at about pH 2.5 to 4.5, most preferably about pH 3.0. Saline (0.9%) that has been adjusted to the appropriate pH (as above) with, for example, 0.1N aqueous hydrochloric acid, may also be used. Most preferably, the pH of the external medium is adjusted by the addition of approximately an equal volume of citric acid solution (pH about 2.5 to about 4.5, preferably 3.0 to the liposome solution. In either case, the final pH of the external liposome solution is from about 2.5 to about 4.5, preferably 3.0–3.5, most preferably 3.0. This citric acid solution may also contain from 5% to 20% by weight of the drying protectant (the saccharide, preferably maltose, at preferably 10% by weight), and preservatives such as BHT and/or EDTA in concentrations acceptable for pharmaceutical products (preferably 0.01% EDTA and 0.02 mg BHT per ml of final solution).

In the case of a relatively acidic first external medium, citric acid phosphate buffer at about pH 5 to about 6, or 0.9% aqueous sodium chloride pH-adjusted to about 3.0 with HCl, or any of the other above-mentioned acidic solutions may be used. The relatively basic medium used to establish the concentration gradient in this case may be phosphate buffer at about pH 8.0, aqueous sodium chloride, (0.9%) adjusted to about pH 7–10 with sodium hydroxide, sodium carbonate, bicarbonate buffer, or any of the above-mentioned basic solutions.

Most preferably, the liposomes are made having an initial basic medium, preferably basic saccharide solution at about pH 7 to about 8, most preferably about pH 7.0. The concentration gradient is established by addition of the second (relatively acidic) buffer, preferably 0.01M citric acid, at pH about 2.5 to 4.5, which when added to the first (relatively basic) external medium, results in a final pH of about 3.0. Such relative basic/relative acidic solution pairs (buffer pairs) enhance the partitioning of the prostaglandin into the liposomes. The concentration gradient may be established either before or after the dehydration or lyophilization, however, as stated above, this dehydration or lyophilization step is preferably performed prior to acidification of the preparation.

In the present invention, the liposomes may alternatively be loaded via a passive technique (no pH gradient) wherein the aqueous solution may comprise aqueous solutions such as distilled water, aqueous buffers, or a drying protectant, for example, a saccharide solution such as dextrose or maltose solution. These methods may include those that form liposomes known as multilamellar vesicles (MLV), stable plurilamellar vesicles (SPLV), large unilamellar vesicles formed by an extrusion procedure (LUVETS), or other liposome-forming procedures known in the art. The process for forming SPLVs is disclosed in Lenk, et al., U.S. Pat. No. 4,522,803, issued June 11, 1985, and the LUVET procedure disclosed in Cullis, et al., PCT Publication No. 86/00238, Jan. 16, 1986, relevant portions of each are incorporated herein by reference. In this case, the liposomes are formed without the benefit of a concentration gradient. In this alternate technique for forming the liposomes of the invention, an aqueous solution containing the drying protectant and the prostaglandin may be added to a dried film comprising any of the suitable lipids used in the invention as discussed hereinabove. Such a lipid film may be coated onto a receptacle such as a tube, a syringe, or a flask. The liposome suspension that results may be dehydrated or lyophilized as previously described.

The lipid to prostaglandin weight ratios used in the present invention can be as high as about 1000:1. Preferably they range from about 1000:1 to about 150:1 more preferably about 900:1 to 200:1; most preferably, about 600:1. Lipid to drug weight ratios of about 150:1 and greater result in entrapment of $PGE_1$ of greater than 60%, and can result in entrapment of 80-100%.

The dehydration or lyophilization of the liposomes of the present invention may be performed by any methods known in the art for dehydrating or lyophilizing liposomes. For dehydration, for example, the liposomes may be dried according to the procedures of Janoff et al., PCT Publication No. 86/01103, Feb. 27, 1986, and incorporated herein by reference.

The liposomes of the invention are preferably lyophilized by pipetting an aliquot of the aqueous-suspended liposomes into serum vials (see Example 9), fitted with lyophilization stoppers and placing them into the lyophilizer. The vials are held for about 1 minute to about 24 hours, preferably about 1 hour at 0° C. to 50° C., preferably about 10° C. The shelf temperature is then decreased to about −12° C. to about −80° C., preferably −40° C., at a rate of about 20° to 0.005° C. per minute, preferably about 1° C. per minute. The vials are held at this temperature for about 0.1 hours to about 120 hours, preferably 3 hours. At about 0.2 hours to about 72 hours, preferably at about 0.6 hours, a vacuum of about 0.0 mm Hg to about 100.0 mm Hg, preferably 0.005 mm Hg is applied. The shelf temperature is then increased to about −40° C. to 0° C., preferably about −25° C., at a rate of about 20° C. to about 0.005° C. per hour referably about 10° C. per hour.

The vials are held at the above temperature (preferably about −25° C.) for about 0.1 to about 120 hours, preferably about 12 hours, after which the shelf temperature is increased to about −20° C. to about 0° C., preferably about −10° C., at a rate of about 20° C. to about 0.005° C. per hour, preferably about 10° C. per hour, and held for about 0.1 to about 120 hours, preferably about 8 hours. The shelf temperature is then increased to about 2° C. to about 40° C., preferably about 10° C., at a rate of about 20° C. to about 0.005° C. per hour, preferably about 10° C. per hour, and held for about 0.1 to about 120 hours, preferably about 8 hours. The shelf temperature is then increased to about 20° C. to about 80° C., preferably about 40° C., and held for about 0.1 to about 120 hours, preferably about 16 hours. Finally, the shelf temperature is decreased to about 5° C. to about 30° C., preferably about 20° C., at a rate of 20° C. to about 0.005° C. per hour, preferably about 10° C. per hour, and this temperature held until stoppering. The vials are then back-flushed with nitrogen, and stoppered.

Regardless of the dehydration of lyophilization technique, the procedure reduces the aqueous content of a sample to less than about 2%, preferably to less than about 1%. Using the current methods, the liposomal prostaglandin formulation is lyophilized to the point of containing 0-2% aqueous content, and preferably 0-1% aqueous (water) content.

The lyophilized prostaglandin-liposome formulations may be stable for at least one year when stored at 6° C. or 25° C. Stability studies are performed according to the methods of Example 14, and employ high pressure liquid chromatography (HPLC) analysis of the formulation. After storage at 6° C. for one year, no degradation products of the $PGE_1$ were present.

When the lyophilized liposomes are to be used, rehydration is accomplished by adding an aqueous solution, e.g., distilled water, water for injection (WFI), or buffer or aqueous solution of appropriate pH, as described above, to the liposomes, and allowing them to sit undisturbed to rehydrate. The liposomes can be resuspended into the aqueous solution by gentle mixing of the solution. The rehydration can be performed at about 25° C. If the prostaglandin was incorporated into the liposomes prior to dehydration, and no further composition changes are desired, the rehydrated liposomes can be used directly in the therapy following known procedures for administering liposome encapsulated drugs.

During preparation of the liposomes, organic solvents may be used to suspend the lipids. Suitable organic solvents are those with a variety of polarities and dielectric properties, which solubilize the lipids, and include but are not limited to methanol, ethanol, dimethylsulfoxide (DMSO), methylene chloride, and solvent mixtures such as hexane:ethanol (95:5). Hexane:ethanol (95:5) is preferably used to initially suspend the lipids, and ethanol is preferably used during the co-mixing of the lipid and the prostaglandin. Solvents are chosen on the basis of their biocompatability, low toxicity, and solubilization abilities.

The liposomes resulting from the processes of the present invention can be used therapeutically in mammals, including man, in the treatment of infections or conditions which require the sustained delivery of the drug in its bioactive form. Such conditions include but are not limited to disease states such as those that can be treated with prostaglandins.

The mode of administration of the preparation may determine the sites and cells in the organism to which the compound will be delivered. The liposomes of the present invention can be administered alone but will generally be administered in admixture with a pharmaceutical carrier selected with regard to the intended route of administration and standard pharmaceutical practice. The preparations may be injected parenterally, for example, intra-arterially or intravenously. The preparations may also be administered via oral, subcutaneous, or intramuscular routes. For parenteral administration, they can be used, for example, in the form of a sterile aqueous solution which may contain other solutes, for example, enough salts or glucose to make the solution isotonic. The prostaglandin $E_1$ liposomes of the present invention, for example, may be given parenterally at a dosage of 5.0 ng per kg body weight per minute, over a two hour period, once or twice a day. Other uses, depending upon the particular properties of the preparation, may be envisioned by those skilled in the art.

For the oral mode of administration, the prostaglandin-liposome compositions of this invention can be used in the form of tablets, capsules, losenges, powders, syrups, elixirs, aqueous solutions and suspensions and the like. In the case of tablets, carriers which can be used include lactose, sodium citrate, and salts of phosphoric acid. Various disintegrants such as starch, and lubricating agents such as magnesium stearate are commonly used in tablets. For administration in capsule form, useful diluents are lactose and high molecular weight polyethylene glycols. When aqueous suspensions are required for oral use, certain sweetening and/or flavoring agents can be added.

For administration to humans in the curative treatment of disease states responding to prostaglandin therapy, the prescribing physician will ultimately determine the appropriate dosage for a given human subject, and this can be expected to vary according to the age, weight, and response of the individual as well as the nature and severity of the patient's disease. The dosage of the drug in liposomal form will generally be about that employed for the free drug. In some cases, however, it may be necessary to administer dosages outside these limits.

The following examples are given for purposes of illustration only and not by way of limitation on the scope of the invention.

EXAMPLE 1

Egg phosphatidylcholine (200 mg) in hexane:ethanol (95:5) was rotary evaporated under reduced pressure in a water bath set at 37° C. to a thin film on the sides of a flask. The film was resuspended in 200.0 ul of ethanol, to which had been added 1.0 mg of $PGE_1$ and 2.0 mg of BHT. This ethanol solution was drawn into a 1.0 ml capacity tuberculin syringe and injected through an 21 gauge needle at about 2 drops/second into a stirring solution of 4.0 ml 10% weight to volume aqueous dextrose solution with 0.01% weight to volume aqueous EDTA, pH 7.0. Upon addition of the ethanol/lipid mixture, the solution became cloudy; this solution was extruded 5 times through a 0.2 um polycarbonate (straight through path type) filter, followed by a second 5 extrusions through a second identical 0.2 um filter The particle size of the resulting liposomes was determined to be 0.24 um±22%, using quasi-elastic light scattering (QELS) (Nicomp Particle Sizer). The suspension was then diluted to 100 ml with 10% dextrose, 0.01% EDTA, pH 7.0, and 1.0 ml aliquots were pipetted into vials and lyophilized according to the procedures of Example 9. The product was rehydrated with 1.0 ml of 0.01M citrate, adjusted to pH 3.0 with sodium hydroxide (NaOH). The resulting pH of the suspension was about 3.0. Entrapment of the $PGE_1$ in the liposomes was determined by HPLC, according to the techniques of Example 8.

EXAMPLE 2

The procedures and materials of Example 1 were used, but after the particle size determination, the suspension was diluted two times with 4.0 ml of 0.01% citric acid containing 10% dextrose and 0.01% EDTA, pH 2.3. This was further diluted to 100 ml with 10% dextrose containing 0.01% EDTA at pH 4.5; the final pH of the suspension was about 3.5. Aliquots (1.0 ml) of this suspension were pipetted into vials, and lyophilized according to the procedures of Example 9. The product was rehydrated with 1.0 ml of distilled water to a final pH of about 3.4. Entrapment was determined according to the techniques of Example 8.

EXAMPLE 3

The procedures and materials of Example 1 were employed using an aqueous stirring solution containing 4.0 ml of 10% dextrose, 0.01% EDTA, and 1% mannitol (total 11% saccharide). Entrapment was determined according to the techniques of Example 8. QELS determined the liposome particle size to be about 0.247 um±10%.

EXAMPLE 4

The procedures and materials of Example 1 were employed using an aqueous stirring solution at pH 7.4. Entrapment was determined according to the techniques of Example 8. QELS determined the liposome particle size to be 0.288 um±44% in diameter.

EXAMPLE 5

The procedures of Example 2 were followed using a stirring aqueous solution of pH 7.4, and 2% mannitol, 10% dextrose, and 0.01% EDTA. Entrapment was determined according to the techniques of Example 8. The particle size of the liposomes as determined by QELS was 0.288 um±44%.

EXAMPLE 6

The procedure and materials of Example 1 were employed using an aqueous stirring solution containing 4.0 ml of 10% dextrose, 0.01% EDTA, and 2% mannitol (total 12% saccharide). Entrapment was determined according to the techniques of Example 8.

EXAMPLE 7

Egg phosphatidylcholine (100 mg) in hexane:ethanol (95:5) was rotary evaporated under reduced pressure to a thin film on the sides of a flask. The film was resuspended by vortical mixing in 1.0 ml of 0.3M citric acid solution (pH 3.0), and allowed to stand one hour at room temperature. The final pH of the liposome solution was 3.5. The suspension was extruded five times through a 0.2 um straight through path polycarbonate filter, and the pH of the resulting suspension adjusted to 6.9 using NaOH. The sample was lyophilized, and rehydrated with water. Association of the $PGE_1$ with the lipid was determined before and after reconstitution by the Ficoll procedure employed in Example 8.

EXAMPLE 8

The liposomes of the Example 1 were suspended in 1.0 ml of aqueous solution and transferred to a 15 ml Corex tube. The vials that had contained the liposomes were washed with 2×5 ml of histopaque Ficoll solution (Sigma Chemical Co.) and mixed with the contents of the Corex tube. The tube was centrifuged at 16,320 xg for 10 minutes in a Sorvall centrifuge. The lipid settled on the top of the Ficoll. All but 0.5–1.0 ml of the bottom wash, and the lipid layer was removed from the tube using a peristaltic pump. Care was taken to ensure that no lipid was left clinging to the micropipette extractor tube. Tetrahydrofuran (THF) (2.5 ml) was added to the lipid layer left in the tube, and mixed thoroughly. This solution was transferred to a 30 ml Corex tube wrapped in foil. The 15 ml Corex tube was washed with 10.0 ml of 0.1% phosphoric acid and the wash added to the liposome solution. An additional 7.0 ml of 0.1% phosphoric acid was added to the liposome solution. This liposome solution was passed through a Sep-Pak $C_{18}$ cartridge that had been prepared by passing 5.0 ml of methanol followed by 10.0 ml of distilled water through it; the PGE$_1$ that dissociates from the lipid is retained in the cartridge. Methanol (7.0 ml) was passed through the Sep-Pak to elute the PGE$_1$, and the PGE$_1$ was collected in a small round-bottom flask. The methanol in the preparation was removed by rotary evaporation under reduced pressure at a temperature below 35° C. The PGE$_1$ was then dissolved with 1.0 ml of the HPLC mobile phase (acetonitrile:dH$_2$O (pH 2.2, with phosphoric acid) 40:60 by volume) which contained an internal standard of beta-naphthol at a concentration of 50 ug/ml. This suspension was then filtered through a 0.45 um syringe-tip filter (Millipore Millex HV$_4$ type) before injecting into the HPLC.

The above procedure was repeated with the liposomes of Examples 2-7 above.

EXAMPLE 9

Split-top, butyl-rubber stoppered, amber lyophilization vials of 5.0 ml capacity were filled with 1.0 ml of aqueous-suspended liposomes, containing entrapped PGE$_1$. These vials were placed on stainless steel trays into a lyophilizer (PV-24 Stokes Lyophilizer) equipped with a Honeywell DCP7700 Digital Control Programmer. The vials were held at 10° C. for one hour. The shelf temperature was then decreased to −40° C. at a rate of 1° C. per minute. The vials were held at −40° C. for three hours with a vacuum of less than 0.005 mm Hg being applied at 0.6 hours, after the temperature of −40° C. was reached. the shelf temperature was then increased to −25° C. at a rate of 10° C. per hour at a vacuum of less than 0.005 mm Hg.

The vials were held at −25° C. for 12 hours at less than 0.005 mm Hg. The shelf temperature was then increased to −10° C. at a rate of 10° C. per hour, and held for 8 hours. The shelf temperature was then increased to +10° C. at a rate of 10° C. per hour and held for 8 hours. the shelf temperature was then increased to 40° C. and held for 16 hours, at less than 0.005 mm Hg. The shelf temperature was finally decreased to 20° C. at less than 0.005 mm Hg at a rate of 10° C. per hour and held until stoppering. The vials were back-flushed with nitrogen and stoppered.

EXAMPLE 10

Egg phosphatidylcholine (41 ml), as a 108 mg/ml solution in hexane:ethanol (95:5), (total 4,428 mg EPC) was measured into a 500 ml capacity round bottom flask, and the hexane:ethanol removed by rotary evaporation in a water bath set to 37° C. Ethanol (2.0 ml) containing 30 mg BHT was added to the flask and the dried lipid film suspended. An additional 1.0 ml of ethanol was added to fully suspend the EPC.

One liter of a 10% maltose solution was prepared and the pH adjusted to 7.4 with 1.0N sodium hydroxide. The solution was sterilized by passing it through a 0.22 um Millipak 40 filter that was pre-wetted with sterile water.

The EPC/BHT/ethanol solution was added dropwise from a 1.0 ml syringe fitted with a 21 gauge needle at a rate of about 1.0 ml/minute, into a stirring solution of about 800 ml of the 10% maltose, into a 2000 ml beaker. This was repeated for the total amount of EPC/BHT/ethanol, about 8.0 ml. After all the lipid was added, the round bottom flask was rinsed with 2 consecutive aliquots of about 3.0 ml of the maltose solution, and added to the beaker of maltose. The solution was brought up to 1000 ml with additional 10% maltose solution.

EXAMPLE 11

The liposomes formed by the process of Example 10 were homogenized using the Gaulin Model 30 CD homogenizer. The liposomes were placed in a 5 L closed reservoir attached with tubing to the Gaulin and a 316 L stainless steel, sanitary shell and tube heat exchanger attached on the downstream end of the Gaulin, to maintain the temperature of the liposome solution at less than 30° C. A nitrogen source (20 psi) was connected to the 5 L reservoir in order to pressure feed the liposomes into the Gaulin. The liposome solution circulated through the Gaulin at a pressure of 14,000 psi for about 4 minutes, at a flow rate of about one half gallon per minute. The liposomes, following the homogenization had a mean diameter of about 150-200 nm, with a range of size distribution of about 20-500 nm, as measured by quasi-elastic light scattering using the Nicomp Particle Sizer (Nicomp Instruments, Inc., Goleta, CA).

EXAMPLE 12

Liposomes (700 ml) homogenized according to the procedures of Example 11 were filtered through a 0.2 um Millipak filter, and set to stir in a 1500 ml beaker on a stir plate. An ethanolic solution of prostaglandin E$_1$ (3.85 mg PGE$_1$ in 1.4 ml ethanol) was added dropwise from a 5.0 ml pipette. After addition of the PGE$_1$, the suspension was sterile filtered through a 0.2 um Millipak filter, and 1.0 ml aliquots were filled into serum vials. The filled vials were lyophilized according to the method of Example 9.

EXAMPLE 13

A vial of the PGE$_1$ liposomes of Example 12 was reconstituted using 1.0 ml sterile citric acid, pH 3.0 and the vial hand shaken to completely resuspend.

EXAMPLE 14

A vial of the lyophilized liposomes of Example 12 was resuspended in 1.0 ml of the mobile phase HPLC standard (60% water, pH 2.2, 40% HPLC grade acetonitrile, containing B-Naphthol at a concentration of 50 ug/ml). The sample was filtered through a Millipore HV$_4$ 0.45 um filter syringe tip filter into a 2.0 ml capacity HPLC vial. The sample was run on the Rainin HPLC using a 50 ul equipment overload onto a 20 ul load loop at a flow rate of 1.25 ml/minute onto a 15 cm reverse phase column (Rainin C-18 column), attached to a Gilson 116 detector set at 205 nm. The chromatograph column was run for 13 minutes. Peaks corresponding to PGE$_1$ and B-naphthol were identified.

The PGE$_1$ concentration of the sample vial was calculated by standard linear regression analysis of peak area, and compared to a PGE$_1$ HPLC standard curve. Three vials were run for each sample tested and the average concentration calculated.

EXAMPLE 15

The method of Example 14 was repeated for the liposomes made according to the methods of Example 1 at 1 week, 2 week, 30 day, 3 month, 6 month, 9 month, and 1 year intervals.

What is claimed is:

1. A liposome composition comprising an arachidonic acid metabolite, a lipid, and a drying-protectant, and wherein the liposomes contain a partition-enhancing buffer.

2. The liposome composition of claim 1 wherein the arachidonic acid metabolite is a prostaglandin.

3. The liposome composition of claim 2 wherein the prostaglandin comprises prostaglandin $E_1$.

4. The liposome composition of claim 1 wherein the liposomes have a transmembrane concentration gradient.

5. The liposome composition of claim 4 wherein the transmembrane concentration gradient is an ion gradient.

6. The liposome composition of claim 5 wherein the ion gradient is a pH gradient.

7. The liposome composition of claim 1 wherein the partition-enhancing buffer comprises drying-protectant solution and citric acid solution.

8. The liposome composition of claim 7 wherein the drying protectant solution is a saccharide solution.

9. The liposome composition of claim 8 wherein the pH of the saccharide solution is about 3.0 to about 11.0.

10. The liposome composition of claim 9 wherein the pH of the saccharide solution is about 7.0.

11. The liposome composition of claim 8 wherein the pH of the citric acid solution is from about 2.5 to about 4.5.

12. The liposome composition of claim 8 wherein the pH of the citric acid solution is about 3.0.

13. The liposome composition of claim 8 wherein the saccharide solution comprises dextrose, sucrose, or maltose.

14. The liposome composition of claim 13 wherein the saccharide comprises maltose.

15. The liposome composition of claim 8 wherein the saccharide solution comprises from about 5% to about 20% saccharide.

16. The liposome composition of claim 15 wherein the saccharide solution comprises from about 10% to about 12% saccharide.

17. The liposome composition of claim 1 wherein the lipid comprises phospholipid.

18. The liposome composition of claim 17 wherein the phospholipid comprises phosphatidylcholine.

19. The liposome composition of claim 18 wherein the phosphatidylcholine comprises egg phosphatidylcholine.

20. The liposome composition of claim 1 wherein the liposomes are from about 20 nm to about 500 nm.

21. The liposome composition of claim 20 wherein the liposomes have a mean diameter of 100 to 200 nm.

22. The liposome composition of claim 20 wherein the composition is lyophilized.

23. The liposome composition of claim 2 wherein the entrapment of the prostaglandin in the liposome is from about 50% to about 100%.

24. A liposome composition comprising prostaglandin $E_1$, egg phosphatidylcholine, and 10% maltose, and wherein the liposomes contain a partition-enhancing buffer.

25. A method of administering the liposome composition of claim 24 comprising injecting the composition intravenously in a patient.

26. A pharmaceutical composition comprising the liposome composition of claim 24 and a pharmaceutically acceptable carrier or diluent.

27. The liposome composition of claim 24 wherein the lipid to prostaglandin weight ratio is from about 300:1 to 1000:1.

28. The liposome composition of claim 27 wherein the lipid to prostaglandin weight ratio is from about 300:1 to 800:1.

29. A lyophilized liposomal-prostaglandin composition comprising a lipid, a prostaglandin, and at least about 10% drying protectant.

30. The lyophilized composition of claim 29 wherein the drying protectant comprises a saccharide.

31. The lyophilized composition of claim 30 wherein the saccharide comprises dextrose, sucrose, or maltose.

32. A method of preparing a liposomal-prostaglandin composition comprising the step of associating the prostaglandin with the liposomes by means of a transmembrane pH gradient.

33. The method of claim 32 wherein the transmembrane pH gradient is obtained by the steps of:
  (a) forming liposomes in a relatively basic aqueous solution;
  (b) adding a prostaglandin to the suspension of step (a) above; and
  (c) acidifying the external medium of the liposomes.

34. The method of claim 33 wherein the liposomes of step (a) are size-reduced.

35. The method of claim 34 wherein the liposomes are size reduced by filtering through a tortuous path type filter.

36. The method of claim 34 wherein the liposomes are size reduced by filtering through a straight path type membrane filter.

37. The method of claim 34 wherein the liposomes are size reduced by homogenization.

38. The method of claim 33 wherein the liposomes are lyophilized.

39. The method of claim 33 wherein the lipid to prostaglandin weight ratio is from about 300:1 to 1000:1.

40. The method of claim 39 wherein the lipid to prostaglandin weight ratio is from about 300:1 to 800:1.

41. A method of preparing a liposomal-prostaglandin composition comprising a lipid, prostaglandin $E_1$, and a drying protectant, comprising the step of admixing an aqueous solution of the drying protectant containing the prostaglandin with a dried lipid film to obtain the liposomal-prostaglandin composition.

42. The method of claim 41 wherein the resulting liposomal-prostaglandin composition is lyophilized.

43. A method of preparing a liposomal-prostaglandin composition comprising a lipid, prostaglandin $E_1$, a drying protectant, and a partition-enhancing buffer, comprising the steps of:
  (a) admixing an ethanolic solution of the lipid with a relatively basic solution of the drying protectant, forming liposomes;
  (b) size reducing the liposomes;
  (c) admixing the liposomes with an ethanolic solution of prostaglandin $E_1$;
  (d) lyophilizing the liposomes of step (c); and
  (e) reconstituting the liposomes with a relatively acidic citric acid solution.

44. The method of step 43 wherein the lipid is egg phosphatidylcholine.

45. The method of step 43 wherein the drying protectant is a saccharide.

46. The method of step 45 wherein the saccharide is dextrose, sucrose, or maltose.

47. The method of claim 46 wherein the saccharide is maltose.

48. The method of claim 43 wherein the liposomes of step (a) are size reduced by homogenization.

49. A pharmaceutical composition comprising the liposomes formed by the method of claim 43 and a pharmaceutically acceptable carrier or diluent.

50. The liposome composition of claim 1 wherein the arachidonic acid metabolite is obtained synthetically or from natural sources.

51. The liposome composition of claim 24 wherein the prostaglandin $E_1$ is obtained synthetically or from natural sources.

* * * * *